(12) United States Patent
Hughes

(10) Patent No.: US 7,858,391 B2
(45) Date of Patent: Dec. 28, 2010

(54) DEVICE AND METHOD FOR HOLDING A CASSETTE FOR LABORATORY SAMPLES

(75) Inventor: Thomas Fergus Hughes, Eastbourne (GB)

(73) Assignee: Raymond A. Lamb Limited, Eastbourne, East Sussex (GB)

( * ) Notice: Subject to any disclaimer, the term of this patent is extended or adjusted under 35 U.S.C. 154(b) by 0 days.

(21) Appl. No.: 12/759,348

(22) Filed: Apr. 13, 2010

(65) Prior Publication Data

US 2010/0194010 A1    Aug. 5, 2010

Related U.S. Application Data

(63) Continuation of application No. 12/300,828, filed as application No. PCT/GB2007/001855 on May 18, 2007, now abandoned.

(30) Foreign Application Priority Data

May 18, 2006    (GB)    ................................ 0609898.2

(51) Int. Cl.
*B41F 17/00*    (2006.01)
(52) U.S. Cl. .......................... 436/174; 422/104; 422/99; 101/43; 101/4
(58) Field of Classification Search .................. None
See application file for complete search history.

(56) References Cited

U.S. PATENT DOCUMENTS 807,547 A * 12/1905 Fliegel ........................ 210/489

| | | |
|---|---|---|
| 3,731,619 A | 5/1973 | Petrikovsky |
| 6,098,839 A | 8/2000 | Hunell |
| 2003/0049178 A1 | 3/2003 | Kiene et al. |

FOREIGN PATENT DOCUMENTS

GB    2 235 163 A    2/1991

OTHER PUBLICATIONS

International Search Report for PCT/GB2007/001855.

* cited by examiner

*Primary Examiner*—Yelena G Gakh
*Assistant Examiner*—Christopher A Hixson
(74) *Attorney, Agent, or Firm*—Fay Sharpe LLP

(57) ABSTRACT

A device for holding a laboratory sample cassette having a marking surface disposed at inclined angle to a main body of the cassette, has a platen with an aperture through which marking of the marking surface can occur. The device also has a receiving surface for receiving one of said cassette which surface is inclined relative to the platen, a step, and a clamp. A receiving cassette is slid down the inclined receiving surface until the cassette engages the stop and so that the marking surface substantially faces the platen and a recess behind the marking surface is aligned with the clamp. A plunger of the clamp is lowered toward the platen and into the recess so that the marking surface is pinned against the platen. The marking surface can then be marked by marking means via the platen aperture. The plunger is then moved away from the platen and the cassette is removed.

24 Claims, 3 Drawing Sheets

1

DEVICE AND METHOD FOR HOLDING A CASSETTE FOR LABORATORY SAMPLES

This application is a continuation application of U.S. Ser. No. 12/300,828, filed Dec. 22, 2008 now abandoned, filed as a 35 U.S.C. 371 National Filing of PCT/GB2007/001855, International Filing Date May 18, 2007, claiming priority of GB 0609898.2, filed May 18, 2006.

The present invention relates to a device and method for holding a laboratory sample cassette having a marking or writing surface disposed at an angle to the main body of the cassette to enable the marking surface of the cassette to be marked.

A tissue processing laboratory sample cassette may have a marking surface disposed generally at an angle of 45° to the main body of the cassette. There are many cassettes on the market that have different physical properties. A clamp used to hold such a cassette so that its marking surface can be marked has to be adjusted to suit cassettes with different physical properties such as their shape.

GB-A-2235163 discloses a device for clamping and marking a laboratory sample cassette having a marking surface disposed at an angle to the main body of the cassette. A vertical hopper holds a stack of unmarked cassettes with each cassette being held at an angle which is greater than the angle of inclination of the marking surface thereof. The unmarked cassettes are gripped by the hopper. An unmarked cassette is fed from the hopper into a clamp which is inclined at the same angle as the marking surface of the cassette so that the marking surface is positioned approximately horizontally at the lowermost portion of the clamp. The cassette is held in the clamp by a resiliently-biased claw and screws in the clamp are then manually adjusted so that the cassette is correctly positioned for marking. Once marked, the cassette is ejected from the clamp and another unmarked cassette is received by the clamp from the hopper.

A problem with the device is that it takes time to manually adjust the screws so that the cassette is correctly positioned before the cassette can be marked.

Another problem is that the marking surface of different laboratory sample cassettes may be at different angles relative to the main bodies thereof. The device can only be effectively used for cassettes, the marking surfaces of which match the incline of the clamp.

Furthermore, different laboratory sample cassettes may have different lengths and a problem may arise that the hopper may not grip unmarked cassettes the lengths of which are significantly shorter than those of the cassettes the hopper is designed to hold as the former may not be held at an angle greater than their inclined marking surface.

It is an object of the present invention to provide a device and method to alleviate the above-mentioned problems.

According to one aspect of the present invention there is provided a device for holding a laboratory sample cassette having a marking or writing surface disposed at an inclined angle to a main body of the cassette, the device comprising:

a platen with a marking region through which marking of the marking surface can occur;

a receiving surface for receiving one said cassette which surface is inclined with respect to the platen;

a stop for a received cassette to rest against; and a clamp arranged to be lowered towards the platen to urge the marking surface against the platen.

The device enables a laboratory sample cassette to be held in a fixed position to enable it to be marked. The device can handle cassettes of different sizes and angles of marking or writing surfaces without requiring manual adjustment of the device.

The device is arranged to hold plastic laboratory cassettes.

The receiving surface is preferably inclined at an angle of less than 45° to the platen. The receiving surface may be inclined at an angle to the platen in the range of 30° to 40° and the angle to the platen may be substantially 35°.

The stop preferably has an inclined surface facing the inclined receiving surface that is inclined in the opposite direction thereto. This enables the edge of the marking surface distal from the main body of the cassette to slide against the inclined surface of the stop when the clamp urges the marking surface towards the platen so that the marking surface of the cassette is aligned with the marking region in the platen.

Preferably, the marking region comprises an aperture for enabling marking means to mark the marking surface of a cassette clamped by the device.

The receiving surface may have guiding means for aligning a received cassette with the marking region in the platen. The stop may have guiding means for aligning a received cassette with the marking region in the platen.

The clamp may comprise at least one plunger and driving means for driving the at least one plunger towards the platen and the driving means may comprise a solenoid. One end of the plunger may comprise a resilient tip arranged to be urged towards the platen.

The receiving surface may be arranged to form the lowermost portion of a cassette receiving chute.

The clamp may include resilient means energisable by the clamp plunger being lowered towards the platen. The device may include release means arranged to release the resilient means or the at least one plunger so that the plunger is moved away from the platen by the de-energisation of the resilient means. The resilient means may comprise a spring which is compressed when the at least one plunger is lowered towards the platen. The release means may comprise the solenoid for driving the at least one plunger and is arranged to release the resilient means when the solenoid is switched from one state to another.

In one embodiment, the device includes retractable positioning means arranged to be moved towards the inclined receiving surface so as to engage the edge of the marking surface distal from the main body of a pinned cassette and/or to urge a cassette against the inclined receiving surface to align the marking surface with the marking region in the platen.

According to another aspect of the present invention there is provided a method for holding a laboratory sample cassette having a marking surface disposed at an inclined angle to a main body of the cassette and a recess behind the marking surface, the method comprising the steps of:

providing a platen with a marking region through which marking of the marking surface can occur, a receiving surface for receiving one said cassette which surface is inclined with respect to the platen, a stop, and a clamp;

sliding a received cassette down the inclined receiving surface until the cassette engages the stop and so that the marking surface substantially faces the platen and the recess behind the marking surface is aligned with the clamp; and lowering the clamp towards the platen and into the recess so that the marking surface is pinned against the platen.

The method may include moving the clamp away from the platen to release the cassette.

Embodiments of the present invention will now be described, by way of example, with reference to the accompanying schematic drawings, in which.

Figure 1:
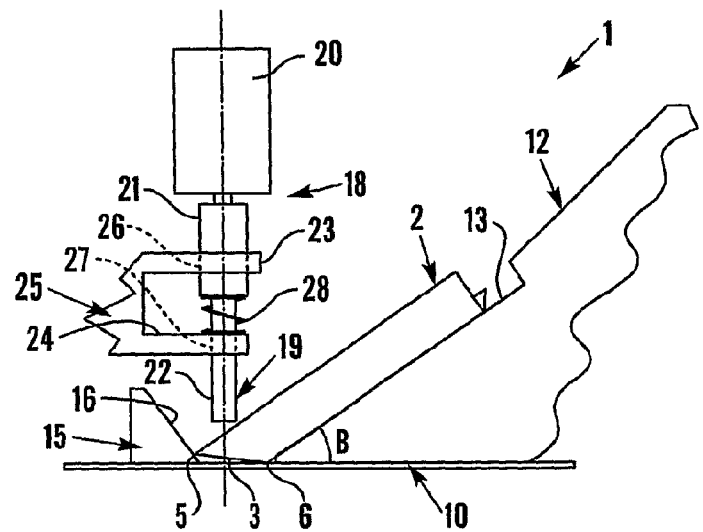
FIG. 1 is a side view of a cassette holding device according to one embodiment of the invention.
Figure 2:
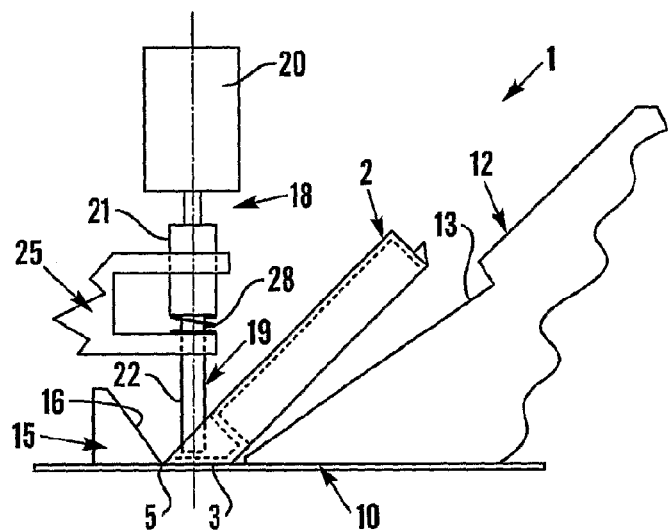
FIG. 2 is a side view of the device showing a clamped cassette.

Referring to FIGS. 1 to 4 of the accompanying drawings, a device 1 is arranged to hold an injection moulded laboratory sample cassette 2 having a writing or marking surface 3 disposed at an inclined angle A to the main body 4 of the cassette 2. The marking surface 3 has an edge 5 distal from the main body 4 of the cassette 2 and the marking surface 3 is inclined from the main body 4 along a shoulder 6 which is opposite, and parallel to, the distal edge 5. The cassette 2 has a hollow space or recess 7 behind the marking surface 3. One side 8 of the recess 7 is perpendicular to the length of the cassette and is perpendicular in relation to the main body 4 of the cassette 2. The opposite side 9 of the recess 7 is parallel to the marking surface 3 and the marking surface 3 and opposite side 9 define opposite sides of a wall 34 of the cassette 2 inclined relative to the main body 4 of the cassette 2.

The device 1 has a thin metal platen 10 with an aperture 11 or cut out forming a marking region through which marking of the cassette marking surface 3 can occur.

A chute 12 is used to deliver cassettes 2 to the device 1. The surface 13 of the bottom portion of the chute 12 is arranged to receive a cassette and is inclined at an angle B of preferably 35° to the platen 10 which is smaller than the angle A of the inclined marking surface 3 of a typical cassette 2 (normally approximately 45°). The bottom portion of the chute 12 has guides 14 on opposite sides of the inclined surface 13 to align the marking surface 3 of the cassette 2 with the platen aperture 11.

Opposite the bottom of the chute 12 is a stop 15 which has an inclined surface 16 facing the chute 12 and is inclined in the opposite direction to the chute 12. The stop 15 has guides 17 on opposite sides of the inclined surface 16 to align the marking surface 3 of the cassette 2 with the platen aperture 11.

Figure 3:
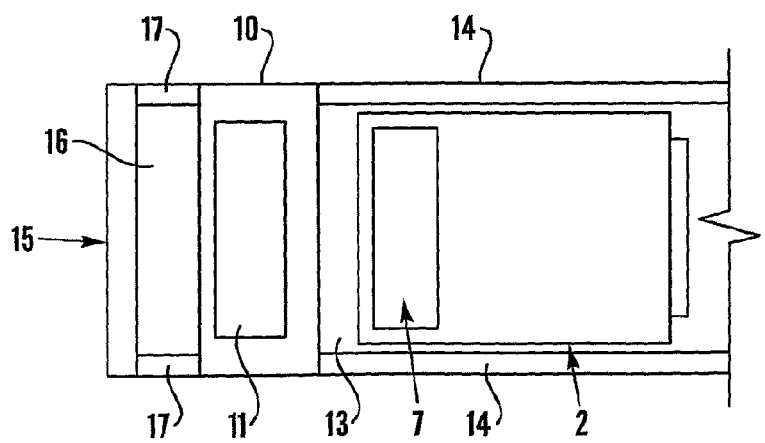
FIG. 3 is a plan view of the device and a cassette.
Figure 4:
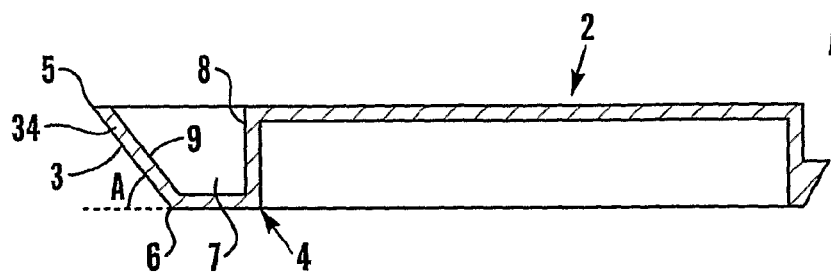
FIG. 4 is a longitudinal cross-section through a cassette.

The guides 14 and 17 have been omitted from the figures other than FIG. 3 for reasons of clarity.

The device 1 has a clamp 18 arranged to be lowered towards the platen 10 and the clamp 18 includes a plunger 19 extending downwardly from a solenoid 20. The plunger 19 has a portion which is of a larger diameter 21 than the rest 22 of the plunger and the plunger 19 is supported by a pair of arms 23, 24 of a bracket 25. The upper arm 23 of the bracket 25 has an aperture 26 for receiving the larger diameter plunger portion 21 and the lower arm 24 of the bracket 25 has an aperture 27 for receiving the smaller diameter plunger portion 22. Between the larger diameter plunger portion 21 and the bracket lower arm 24 is a resilient compression spring 28 surrounding the smaller diameter plunger portion 22.

In use, a laboratory sample cassette 2 is delivered by gravity and slides down the chute 12. The cassette point, which is the distal edge 5 of the marking surface 3, engages the inclined surface 16 of the stop 15 so that the cassette marking surface 3 substantially faces the platen 10 and the recess 7 behind the marking surface 3 is aligned with the clamp 18.

The clamp solenoid 20 is switched on to lower the plunger 19 towards the platen 10 and as the plunger 19 is lowered the larger diameter plunger portion 21 compresses the spring 28 against the lower bracket arm 24 and energises the spring 28. The plunger 19 is lowered into the cassette recess 7 so that it engages the recess side 9 on the opposite side of the cassette 2 to the marking surface 3 causing the marking surface 3 to be pinned against the platen 10. This pivots the cassette 2 about its shoulder 6 and lifts the bottom of the cassette off the cassette receiving surface 13 of the bottom portion of the chute 12 as the receiving surface 13 is inclined at a smaller angle B to the platen 10 than the angle A of the inclined marking surface 3 of the cassette 2. The lowering plunger 19 also causes the cassette distal edge 5 to slide down to the bottom of the inclined surface 16 of the stop 15 so that the cassette 2 is correctly aligned with the device 1 with the marking surface 3 being aligned with the platen aperture 11.

The marking surface 3 is then marked by marking means (not shown) which may comprise applying foil tape to the underside of the platen 10 covering the aperture 11 and applying a stylus to the part of the foil tape covering the aperture 11 to mark the aligned marking surface 3 of the cassette 2 on the other side of the tape using a hot foil technique.

When the cassette 2 has finished being marked, the clamp solenoid 20 is switched off causing the plunger 19 to move away from the platen 10 by the de-energisation of the spring 28. The cassette 2 falls back on to the inclined cassette receiving surface 13 from where the cassette 2 can be ejected from the device 1, and another unmarked cassette can then be delivered into the device 1 via the chute 12.

Figure 5:
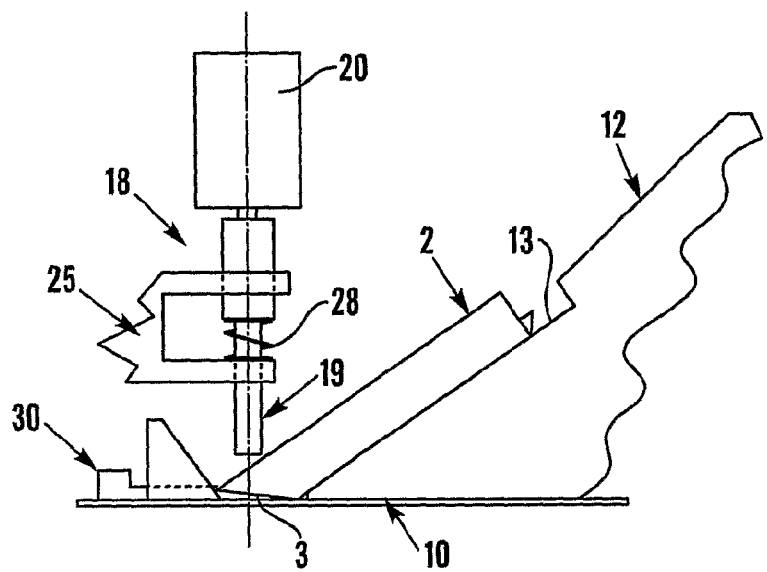
FIG. 5 is a side view of a cassette holding device according to another embodiment of the invention.
Figure 6:
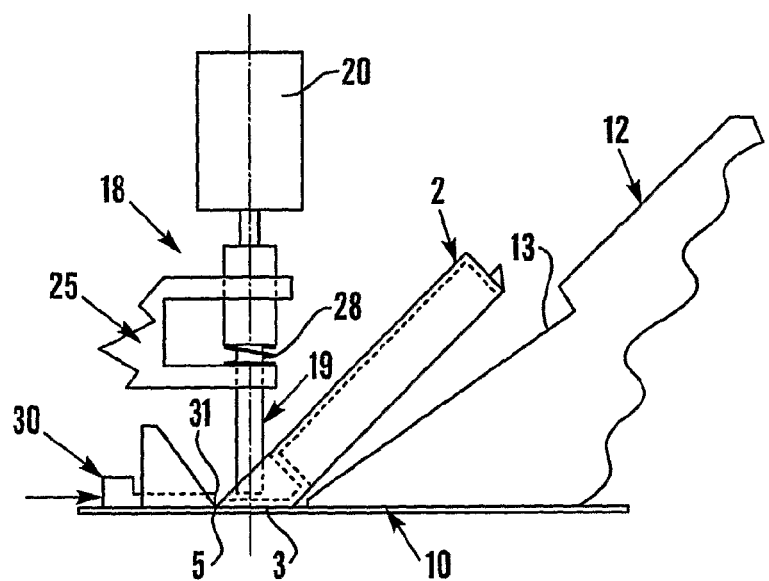
FIG. 6 is a schematic side view of the device of FIG. 5 showing a clamped cassette.

In a modification shown in FIGS. 5 and 6, a retractable positioner 30 has an engaging face 31 which is parallel to the platen aperture 11. The positioner 31 is arranged to be driven under the stop 32 along a line coincident with the centre-line of the chute 33 (see FIG. 3) so that its engaging face 31 engages the cassette distal edge 5 whilst the marking surface 3 of the cassette 2 is pinned to the platen 10 by the clamp plunger 19. As the engaging face 31 is pushed against the distal edge 5, the distal edge 5 becomes aligned with the engaging face 31 ensuring that the marking surface 3 is aligned with the platen aperture 11. The retractable positioner 30 may urge the cassette 2 against the inclined receiving surface 13 of the chute 12.

Figure 7:
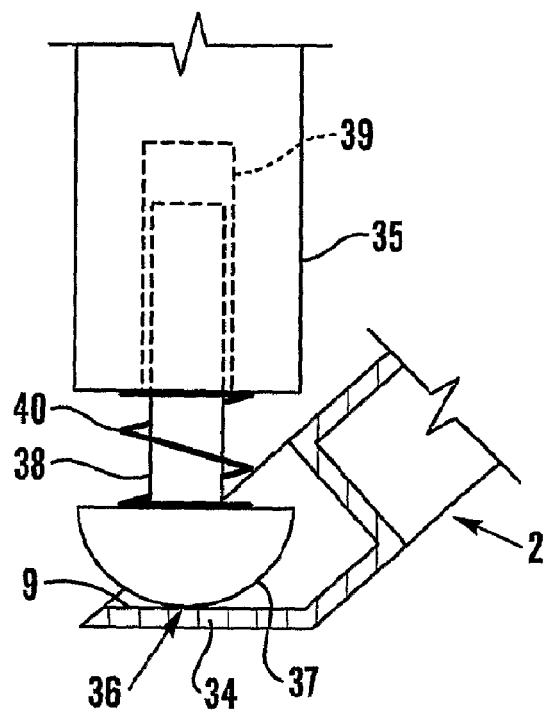
FIG. 7 is a detail of a modified plunger forming part of a clamp of the cassette holding device.

In another embodiment shown in FIG. 7, the end of a plunger 35 engaging the recess side 9 of the cassette 2 has a resilient tip 36 which is spring loaded to enable the plunger 35 to adjust to any variance in the thickness of the inclined wall 34 of the injection moulded laboratory sample cassette 2. The tip 36 has a head 37 at the end of a column 38 extending into a shaft 39 in the plunger 35 and a resilient compression spring 40 surrounding the column 38 and fixed between the head 37 and the plunger 35.

Figure 8:
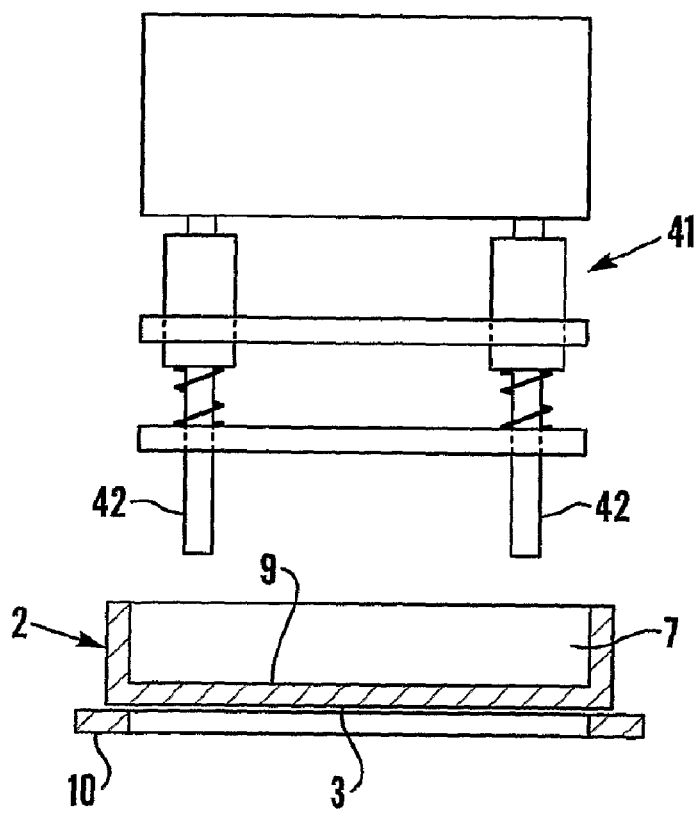
FIG. 8 is an elevational view of a modified clamp.

In yet another embodiment shown in FIG. 8, the clamp 41 has a pair of parallel plungers 42 with both plungers 42 arranged to be lowered into the cassette recess 7 and engage the recess side 9 to cause the marking surface 3 of the cassette 2 to be pinned against the platen 10. When a cassette 2 has finished being marked the plungers 42 are moved away in the same way as previously described for a single plunger 19.

Whilst particular embodiments have been described, it will be understood that various modifications may be made without departing from the scope of the invention. For example, the clamp may have any suitable number of plungers arranged in any appropriate way to cause the marking surface 3 of the cassette 2 to be pinned against the platen 10. Any number of the plungers may have spring loaded tips 36.

The invention claimed is:

1. A device for holding a laboratory sample cassette having a marking surface disposed at an inclined angle (A) to a main body of the cassette, the device comprising:
    a platen with a marking region through which marking of the marking surface can occur;
    a marking member operatively associated with the platen marking region for marking the marking surface;
    a receiving surface for receiving one said cassette which receiving surface is inclined with respect to the platen;
    a stop for a received cassette to rest against; and
    a clamp arranged to be lowered towards the platen along a line substantially normal to a plane defined by the platen to urge the marking surface against the platen.

2. The device as claimed in claim 1, wherein the receiving surface is inclined at an angle of less than 45° to the platen.

3. The device as claimed in claim 1, wherein the receiving surface is inclined at an angle in the range of 30° and 40° to the platen.

4. The device as claimed in claim 1, wherein the receiving surface is inclined at an angle of substantially 35° to the platen.

5. The device as claimed in claim 1, wherein the stop has an inclined surface facing the inclined receiving surface that is inclined in the opposite direction thereto.

6. The device as claimed in claim 1, wherein the marking region comprises an aperture for enabling marking means to mark the marking surface of a cassette clamped by the device.

7. The device as claimed in claim 1, wherein the receiving surface has means for aligning a received cassette with the marking region in the platen.

8. The device as claimed in claim 1, wherein the stop has means for aligning a received cassette with the marking region in the platen.

9. The device as claimed in claim 1, wherein the receiving surface is arranged to form the lowermost portion of a cassette receiving chute.

10. The device as claimed in claim 1, including retractable positioning means arranged to be moved towards the inclined receiving surface so as to engage the edge of the marking surface distal from the main body of a pinned cassette.

11. The device as claimed in claim 1, including retractable positioning means arranged to urge a received cassette against the inclined receiving surface.

12. The device as claimed in claim 1, wherein the clamp includes resilient means energisable by the clamp being lowered towards the platen.

13. The device as claimed in claim 1, wherein the clamp comprises at least one plunger and means for driving the at least one plunger towards the platen.

14. The device as claimed in claim 12, including release means arranged to release the resilient means or the at least one plunger so that the at least one plunger is moved away from the platen by the de-energisation of the resilient means.

15. The device as claimed in claim 13, wherein the driving means comprises a solenoid.

16. The device as claimed in claim 14, wherein the release means comprises the solenoid and is arranged to release the resilient means when the solenoid is switched from one state to another.

17. The device as claimed in claim 12, wherein one end of the plunger comprises a resilient tip arranged to be urged towards the platen.

18. The device as claimed in claim 12, wherein the resilient means comprises a resilient spring which is compressed when the at least one plunger is lowered towards the platen.

19. A method for holding a laboratory sample cassette having a marking surface disposed at an inclined angle to a main body of the cassette and a recess behind the marking surface, the method comprising the steps of:
    providing a platen with a marking region through which marking of the marking surface can occur, a receiving surface for receiving one said cassette which surface is inclined with respect to the platen, a stop, and a clamp;
    sliding a received cassette down the inclined receiving surface until the cassette engages the stop and so that the marking surface substantially faces the platen and the recess behind the marking surface is aligned with the clamp; and
    lowering the clamp towards the platen and into the recess so that the marking surface is pinned against the platen, wherein the clamp is lowered substantially perpendicularly to the platen and at an inclined angle to the receiving surface wherein the included angle is the complement of the angle between the receiving surface and the platen.

20. The method as claimed in claim 19, wherein the method includes moving the clamp away from the platen to release the cassette.

21. The method as claimed in claim 19, wherein the method includes providing the stop with an inclined surface facing the inclined receiving surface and inclined in the opposite direction, and the step of lowering the clamp includes sliding the edge of the marking surface distal from the main body of the cassette against the inclined surface of the stop so that the marking surface is aligned with the marking region of the platen.

22. The method as claimed in claim 19, including moving retractable positioning means towards the inclined receiving surface so as to engage the edge of the marking surface distal from the main body of a pinned cassette.

23. The method as claimed in claim 19, including urging a received cassette against the inclined receiving surface in order to align the cassette with the marking region of the platen.

24. The device as claimed in claim 2, wherein the stop has an inclined surface facing the inclined receiving surface that is inclined in the opposite direction thereto.

* * * * *